United States Patent [19]

Meyers et al.

[11] 4,224,199
[45] Sep. 23, 1980

[54] SOMATOSTATIN ANALOGS HAVING A SUBSTITUTED TRYPTOPHYL RESIDUE IN POSITION EIGHT

[76] Inventors: Chester A. Meyers, 120 Maple Cir., Slidel, La. 70458; David H. Coy, 4319 Perrier St., New Orleans, La. 70115; Andrew V. Schally, 5025 Kawanee Ave., Metairie, La. 70002

[21] Appl. No.: 28,477

[22] Filed: Apr. 9, 1979

[30] Foreign Application Priority Data

May 19, 1978 [CA] Canada ................................. 303800

[51] Int. Cl.² .................... C08L 37/00; C07C 103/52; A61K 37/00
[52] U.S. Cl. ................................ 260/8; 260/112.5 S; 424/177
[58] Field of Search ............................. 260/8, 112.5 S; 424/177

[56] References Cited

PUBLICATIONS

J. Rivier, et al., Biochem. Biophys. Res. Commun., 65, 746 (1975).
D. H. Coy, et al., Endocrinology 98, 305A (1976).
D. H. Coy, et al., Biochemistry 13, 3550 (1974).
Meyers, et al., Biochemistry, 2326–2330, 1978.

*Primary Examiner*—Delbert R. Phillips
*Attorney, Agent, or Firm*—Arthur E. Wilfond

[57] ABSTRACT

Tetradecapeptides of the formula

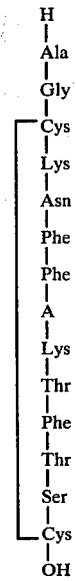

in which A represents L, D or DL 5- or 6- fluoro-, bromo-,chloro- or iodotryptophyl, or a therapeutically acceptable acid addition salt thereof, their preparation and intermediates for their preparation are disclosed. The tetradecapeptides are useful for inhibiting the release of growth hormone. Compositions and methods for their use also are disclosed.

17 Claims, No Drawings

SOMATOSTATIN ANALOGS HAVING A SUBSTITUTED TRYPTOPHYL RESIDUE IN POSITION EIGHT

The invention described herein was made in the course of work under a grant or award from the Department of Health, Education and Welfare.

BACKGROUND OF THE INVENTION (a) Field of Invention

This invention relates to analogs of the tetradecapeptide somatostatin. More particularly, this invention concerns somatostatin analogs in which the tryptophyl residue at position eight is replaced by a tryptophyl residue having a fluoro, bromo, chloro or iodo substituent at position 5 or 6 of the indole ring system and salts thereof, a process for preparing the analogs and salts, intermediates used in the process and methods for using the somatostatin analogs and their salts.

(b) Prior Art

The name "somatostatin" has been proposed for the factor found in hypothalamic extracts which inhibits the secretion of growth hormone (somatotropin). The structure of this factor has been elucidated by P. Brazeau et al., Science, 179, 77(1973) and reported to have the following tetradecapeptide structure:

The constitution of the tetradecapeptide somatostatin has been confirmed by synthesis; for example, see D. Sarantakis and W. A. McKinley, Biochem. Biophys. Res. Comm., 54, 234(1973) and H. U. Immer et al., Helv. Chim. Acta, 57, 730(1974).

The important physiological activity of this tetradecapeptide established it as a compound of significance for clinical pharmacology relating to the treatment of acromegaly and the management of diabetes; for example, see K. Lundbaek et al., Lancet, 2, 131(1970) and A. Gordin et al., Acta Endocrinologica, 86, 833–841(1977).

Since the structure and physiological activity of somatostatin were determined, a number of somatostatin analogs have been reported. One of the more important analogs, [D-Trp]$^8$-somatostatin, reported by J. Rivier et al., Biochem. Biophys. Res. Commun., 65, 746(1975) and D. H. Coy et al., Endocrinology, 98, 305A(1976), is five to eight times more active than somatostatin on the inhibition of growth hormone release in vitro.

The present invention discloses novel somatostatin analogs in which the tryptophyl residue at position eight is replaced by a tryptophyl residue having a fluoro, bromo, chloro or iodo substituent at position 5 or 6 of the indole ring system. Surprisingly, the somatostatin analogs of the present invention have been found to be more active in inhibiting growth hormone in vitro than the corresponding natural somatostatin or [D-Trp]$^8$-somatostatin. This result indeed is surprising and unexpected in view of the fact that replacement of a tryptophyl residue with a substituted tryptophyl in other hypothalamic releasing hormones has resulted in a reduction of biological activity. For example, the [5F-Trp]$^3$-LH-RH analog, is reported by D. H. Coy et al., Biochemistry, 13, 3550(1974). In the latter instance the analog exhibits only six percent of the activity of the natural LH-RH.

SUMMARY OF THE INVENTION

The somatostatin analogs of this invention are represented by the tetradecapeptides of formula I,

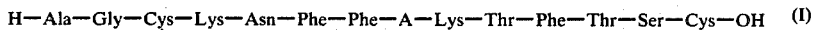

in which A represents L, D or DL 5- or 6-fluoro-, bromo-, chloro- or iodo-tryptophyl, or a therapeutically acceptable acid addition salt thereof.

Preferred somatostatin analogs are represented by the tetradecapeptides of formula I

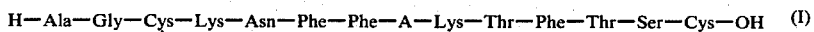

in which A represents L or D 5- or 6-fluoro- or bromo-tryptophyl, or a therapeutically acceptable acid addition salt thereof.

Also included within the scope of this invention are the peptide intermediates of formula II

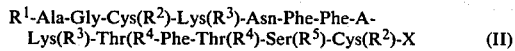

in which A is as defined herein; $R^1$ is hydrogen or an α-amino protecting group; $R^2$ is hydrogen or a sulfhydryl protecting group; $R^3$ is hydrogen or an ε-amino protecting group; $R^4$ and $R^5$ each is hydrogen or a hydroxy protecting group; and X is hydroxy or O-CH$_2$-[resin], with the proviso that: when X is hydroxy, then $R^1$, $R^2$, $R^3$, $R^4$ and $R^5$ are hydrogen; and when X is O-CH$_2$-[resin], then $R^1$, $R^2$, $R^3$, $R^4$ and $R^5$ each are other than hydrogen.

A preferred group of intermediates of formula II are those in which A is as defined herein; $R^1$, $R^2$, $R^3$, $R^4$ and $R^5$ are hydrogen; and X is hydroxy.

Another preferred group of intermediates of formula II are those in which A represents L, D or DL 5- or 6-fluoro- or bromo-tryptophyl; $R^1$ is hydrogen or t-butoxycarbonyl; $R^2$ is hydrogen or 4-methylbenzyl; $R^3$ is hydrogen or 2-chlorobenzyloxycarbonyl; $R^4$ and $R^5$ each is hydrogen or benzyl; X is hydroxy or O-CH$_2$-[polystyrene-1%-divinylbenzene resin], with the proviso that: when X is hydroxy, then $R^1$, $R^2$, $R^3$, $R^4$ and $R^5$ are hydrogen; and when X is O-CH$_2$-[polystyrene- 1%-divinylbenzene resin], then $R^1$, $R^2$, $R^3$, $R^4$ and $R^5$ are other than hydrogen.

Still another preferred group of intermediates of formula II are those in which A represents L, D or DL 5- or 6-fluoro- or bromo-tryptophyl; $R^1$, $R^2$, $R^3$, $R^4$ and $R^5$ are hydrogen; and X is hydroxy.

DETAILS OF THE INVENTION

In general the abbreviations used herein for designating the amino acids and the protective groups are based on recommendations of the IUPAC-IUB Commision of Biochemical Nomenclature, see Biochemistry, 11, 1726–1732(1972). For instance, Ala, Gly, Cys, Lys, Asn, Asp, Phe, Trp, L-Trp, D-Trp, DL-Trp, D-5-Br-Trp, L-6-F-Trp, Thr and Ser represent the "residues" of L-alanine, glycine, L-cysteine, L-lysine, L-asparagine, L-aspartic acid, L-phenylalanine, L-tryptophan, L-tryptophan, D-tryptophan, DL-tryptophan, D-5-bromotryptophan, L-6-fluorotryptophan, L-threonine and L-serine, respectively. The term "residue" refers to a radical derived from the corresponding α-amino acid by eliminating the hydroxyl of the carboxyl group and one hydrogen of the α-amino group.

A number of procedures or techniques for the preparation of peptides have hitherto been well established and found in general textbooks of peptide chemistry; for example, K. D. Kopple, "Peptides and Amino Acids", W. A. Benjamin, Inc., New York, 1966, pp. 33–51 and E. Schröder and K. L. Lübke, "The Peptides" Vol. I, Academic Press, New York, 1965, pp. 3–128. For instance, the functional groups which are not involved in the peptide bond formation reaction are protected by a protecting group or groups introduced prior to the condensation reaction. Examples of protecting groups for an amino group, herein referred to as an α-amino protecting group, not involved in the peptide bond formation are: the urethane type which includes benzyloxycarbonyl (represented by Z), t-butoxycarbonyl (represented by Boc), α,α-dimethyl-3,5-dimethyoxybenzyloxycarbonyl (represented by Ddz), 2-(4-biphenyl)-isopropyloxycarbonyl (represented by Bpoc), 4-nitrobenzyloxycarbonyl, isonicotinyloxycarbonyl, isobornyloxycarbonyl, isopropyloxycarbonyl, or ethoxycarbonyl; the acyl type protecting groups which include formyl, trifluoroacetyl, phthalyl, acetyl (Ac), nitrophenylsulfenyl, or toluenesulfonyl; the alkyl type protecting groups which include triphenylmethyl (or trityl, represented by Trt) trimethylsilyl or benzyl; the preferred α-amino protecting group defined by $R^1$ is t-butoxylcarbonyl. The requirement for selecting an α-amino protecting group being that the conditions of its removal should not affect any other portion of the peptide, i.e. peptide linkages, other protecting groups, the resin or cause racemization of an amino acid residue.

The term "sulfhydryl protecting group" refers to the protecting group for the sulfhydryl on cysteine. Suitable sulfhydryl protecting groups can be selected from 4-methoxybenzyl, 4-methylbenzyl, benzyl, benzhydryl, acetamidomethyl, trityl, 4-nitrobenzyl, t-butyl, isobutoxymethyl, as well as any of a number of trityl derivatives. For additional groups, see, for example Houben-Weyl, Methodes der Organischen Chemie, "Synthese von Peptiden", Vols. 15/1 and 15/2, (1974) Stuttgard, Germany. Preferably, the sulfhydryl protecting group defined by $R^2$ is 4-methylbenzyl.

The term "ε-amino protecting group" refers to the protecting group on the ε-amino function of lysine and illustrative of such groups are benzyloxycarbonyl, t-butoxycarbonyl, t-amyloxycarbonyl, cyclopentyloxycarbonyl, adamantyloxycarbonyl, 4-methoxybenzyloxycarbonyl, 2-chlorobenzyloxycarbonyl, 2,6-dichlorobenzyloxycarbonyl, 2,4-dichlorobenzyloxycarbonyl, 2-bromobenzyloxycarbonyl, 4-nitrobenzyloxycarbonyl, isopropoxycarbonyl, cyclohexyloxycarbonyl, cycloheptyloxycarbonyl, p-toluenesulfonyl, and the like. The preferred ε-amino protecting group defined by $R^3$ is 2-chlorobenzyloxycarbonyl.

The term "hydroxy protecting group" refers to the protecting group for the hydroxy on serine or threonine and illustrative of such groups are $C_1-C_4$ alkyl, such as methyl, ethyl, t-butyl, and the like; benzyl; substituted benzyl, such as 4-methoxybenzyl, 4-nitrobenzyl, 4-chlorobenzyl, and the like; $C_1-C_3$ alkanoyl, such as formyl, acetyl, and propionyl; triphenylmethyl(trityl); and the like. Preferred hydroxy protecting group defined by $R^4$ and $R^5$ is benzyl.

The tetradecapeptides of this invention can be obtained in the form of the free base or in the form of a therapeutically acceptable acid addition salt. The peptides in the form of the free bases are readily obtained from the corresponding acid addition salt by conventional methods, for example, a solution of the acid addition salt is passed through an anionic exchange resin (OH$^-$ form) to obtain the free base. The free base is also obtained from the acetic acid addition salt by repeated lyophilization of the latter salt from aqueous solution. The acetic acid addition salt is readily obtained from other acid addition salt by treatment with the appropriate ion exchange resin, for example, Sephadex TM G-15 using 50% acetic acid in the manner described by D. H. Coy, et al., Biochem. Biophys. Res. Commun., 1267–1273(1973), incorporated herein by reference. The peptides of this invention are obtained in the form of a therapeutically acceptable acid addition salt either directly from the process of this invention or by reacting the peptide with one or more equivalents of the appropriate acid. Examples of preferred non-toxic salts are those with therapeutically acceptable organic acids, e.g., acetic, lactic, succinic, benzoic, salicyclic, methanesulfonic, toluenesulfonic, or pamoic acid, as well as polymeric acids such as tannic acid or carboxymethyl cellulose, and salts with inorganic acids such as the hydrohalic acids, e.g., hydrochloric acid, or sulfuric acid, or phosphoric acid.

The peptides produced by the process of this invention, as well as their corresponding therapeutically acceptable acid addition salts, are useful because they possess the pharmacological activity of the natural tetradecapeptide somatostatin. Their activity is demonstrated readily in pharmacological tests such as a modification [A. V. Schally et al., Bichem. Biophys. Res. Commun., 52, 1314(1973) and J. Rivier et al., C.R. Acad. Sci. Paris, Ser. D, 276, 2737(1973)] of the in vitro method of M. Saffran and A. V. Schally, Can. J. Biochem. Physiol., 33, 405(1955).

The activity of the tetradecapeptides of this invention to inhibit growth hormone release in vitro is demonstrated by the method described by C. Meyers et al., Biochem. Biophys. Res. Commun., 74, 630(1977). In this method, the tetradecapeptides of this invention are shown to inhibit the release of radioimmunoassayable growth hormone in vitro from enzymatically dispersed rat anterior pituitary cells prepared as described by F. Labrie et al., Sixth Karolinska Symp. on Res. Meth. in Reprod. Endocrinol. (W. Dozfalusy, Ed.), pp 301–328(1973). Following four days in culture, the cells are washed and incubated for five hours at 37° C. in Dulbecco-modified Eagle's medium in the presence or absence of increasing concentrations of each tetradecapeptide analog. Growth hormone levels are determined by double antibody radioimmunoassay, method described by C. A. Birge et al., Endocrinol., 81, 195-204(1967), for rat growth hormone using the NIAMDD Rat GH RIA kit. The dose required for a 50% inhibition of growth hormone release ($ED_{50}$) is calculated for each analog by the method of D. Rodbard, Endocrinol., 94, 1427-1437(1974). The potency of the tetradecapeptide analogs of this invention relative to somatostatin is illustrated in table I.

TABLE I
IN VITRO GROWTH HORMONE RELEASE-INHIBITING ACTIVITIES OF THE "SOMATOSTAIN" ANALOGS OF THIS INVENTION

| Somatostatin Analog of formula I | | Growth Hormone Release-Inhibiting Activity, Relative to Somatostatin % |
|---|---|---|
| A | Described in Example | |
| L-5-Br-Trp | 5 | 548 |
| D-5-Br-Trp | 5 | 3002 |
| L-6-F-Trp | 6 | 118 |
| D-6-F-Trp | 6 | 846 |
| L-5-F-Trp | 7 | 476 |
| D-5-F-Trp | 7 | 2499 |

The somatostatin analogs of this invention or the acid addition thereof are useful for the treatment of acromegaly and related hypersecretory endocrine states and in the management of diabetes in mammals; see for example, C. Meyers et al., cited above. When the tetradecapeptides or salts thereof are employed for such treatment or management, they are administered systemically, preferably parenterally, in combination with a pharmaceutically acceptable liquid carrier. The tetradecapeptides have a low order of toxicity. The proportion of the tetradecapeptide or salt thereof is determined by its solubility in the given carrier, by the given carrier, or by the chosen route of administration. When the tetradecapeptide or a salt thereof is used in a sterile aqueous solution, such solution may also contain other solutes such as buffers or preservatives, as well as sufficient amounts of pharmaceutically acceptable salts or glucose to make the solution isotonic. The dosage will vary with the form of administration and with the particular species to be treated. Preferably, the dose range for sublingual or oral administration is about 1 mg. to about 100 mg/Kg. of body weight per day. Generally, the dose range for intravenous, subcutaneous, or intramuscular administration is from about 0.1 µg. to about 1 mg/Kg. of body weight per day, and, preferably, is from about 0.5 µg. to about 100 µg/Kg. of body weight per day. It is evident that the dose range will vary widely dependent upon the particular condition which is being treated as well as the severity of the condition.

The tetradecapeptides or salts thereof can also be administered in one of the long-acting, slow-releasing or depot dosage forms described below, preferably by intramuscular injection or by implantation. Such dosage forms are designed to release from about 0.1 µg to about 50 µg per kilogram body weight per day.

It is often desirable to administer the tetradecapeptide continuously over prolonged periods of time in long-acting, slow-release or depot dosage forms. Such dosage forms may either contain a pharmaceutically acceptable salt of the peptide having a low degree of solubility in body fluids, for example, one of those salts described below, or they may contain the peptide in the form of a water-soluble salt together with a protective carrier which prevents rapid release. In the latter case, for example, the peptide may be formulated with a non-antigenic partially hydrolyzed gelatin in the form of a viscous liquid; or the peptide may be adsorbed on a pharmaceutically acceptable solid carrier, for example, zinc hydroxide, and may be administered in suspension in a pharmaceutically acceptable liquid vehicle; or the peptide may be formulated in gels or suspensions with a protective non-antigenic hydrocolloid, for example, sodium carboxymethylcellulose, polyvinylpyrrolidone, sodium alginate, gelatin, polygalacturonic acids, for example, pectin, or certain mucopolysaccharides, together with aqueous or non-aqueous pharmaceutically acceptable liquid vehicles, preservatives, or surfactants. Examples of such formulations are found in standard pharmaceutical texts, e.g., in Remington's Pharmaceutical Sciences, 14th Ed., Mack Publishing Co., Easton, Pa., 1970. Long-acting, slow-release preparations of the peptide produced according to the process of this invention may also be obtained by microencapsulation in a pharmaceutically acceptable coating, for example, gelatin, polyvinyl alcohol or ethyl cellulose. Further examples of coating materials and of the processes used for microencapsulation are described by J. A. Herbig in "Encyclopedia of Chemical Technology", Vol. 13, 2nd Ed., Wiley, New York, 1967, pp. 436-456. Such formulations, as well as suspensions of salts of the peptide which are only sparingly soluble in body fluids, for example, salts with pamoic acid or tannic acid, are designed to release from about 0.1 µg to about 100 µg of the active compound per kilogram body weight per day, and are preferably administered by intramuscular injection. Alternatively, some of the solid dosage forms listed above, for example, certain sparingly water-soluble salts or dispersions in or adsorbates on solid carriers of salts of the peptide, for example, dispersions in a neutral hydrogel of a polymer of ethylene glycol methacrylate or similar monomers cross-linked as described in U.S. Pat. No. 3,551,556, may also be formulated in the form of pellets releasing about the same amounts as shown above and may be implanted subcutaneously or intramuscularly.

Process

Although the selection of the particular protecting groups to be employed in preparing the compounds of this invention remains a matter well within the ordinary skill of a peptide chemist, it is well to recognize that the proper selection of the protecting groups is dependent upon the particular succeeding reactions which must be carried out. Thus, the protecting group of choice must be one which is stable both to the reagents and under the conditions employed in the succeeding steps of the reaction sequence. For example, as already discussed to some degree hereinabove, the particular protecting group which is employed must be one which remains intact under the conditions which are employed for cleaving the α-amino protecting group of the terminal amino acid residue of the peptide fragment in preparation for the coupling of the next succeeding amino acid fragment to the peptide chain. It is also important to select, as protecting group, one which will remain intact during the building of the peptide chain and which will be readily removable upon completion of the synthesis of the desired tetradecapeptide product. All of these matters are well within the knowledge and understanding of a peptide chemist of ordinary skill in the art.

As is evident from the above discussion, the tetradecapeptides of this invention can be prepared by solid phase synthesis. This synthesis involves a sequential building of the peptide chain beginning at the C-terminal end of the peptide. Specifically, cysteine first is linked at its C-terminal to the resin by reaction of an amino-protected, S-protected cysteine with a chloromethylated resin or a hydroxymethyl resin. Preparation of a hydroxymethyl resin is described by Bodanszky et al., Chem. Ind. (London), 38 1597–98(1966). The chloromethylated resin is commercially available from Lab Systems Inc., San Mateo, Calif.

In accomplishing linkage of the carboxyl of the cysteine to the resin, the protected cysteine first is converted to its cesium salt. This salt then is reacted with the resin in accordance with the method described by B. F. Gisin, Helv. Chim. Acta, 56, 1476(1973). Alternatively, the cysteine can be linked to the resin by activation of the carboxyl function of the cysteine molecule by application of readily recognized techniques. For example, the cysteine can be reacted with the resin in the presence of a carboxyl group activating compound such as N,N'-dicyclohexylcarbodiimide (DCC) or N,N'-diisopropylcarbodiimide.

Once the C-terminal cysteine has been appropriately linked to the resin support, the remainder of the peptide building sequence involves the step-wise addition of each amino acid to the N-terminal portion of the peptide chain. Necessarily, therefore, the particular sequence which is involved comprises a cleavage of the α-amino protecting group from the amino acid which represents the N-terminal portion of the peptide fragment followed by coupling of the next succeeding amino acid residue to the now free and reactive N-terminal amino acid. Cleavage of the α-amino protecting group can be effected in the presence of an acid such as hydrobromic acid, hydrochloric acid, trifluoroacetic acid, p-toluenesulfonic acid, benzenesulfonic acid, naphthalenesulfonic acid, and the like, with formation of the respective acid addition salt product. Another method which is available for accomplishing cleavage of the amino protecting group involves the use of boron trifluoride. For example, boron trifluoride diethyl etherate in glacial acetic acid will convert the amino-protected peptide fragment to $BF_3$ complex which then can be converted to the deblocked peptide fragment by treatment with a base such as aqueous potassium bicarbonate. Any of these methods can be employed as long as it is recognized that the method of choice must be one which accomplishes cleavage of the N-terminal α-amino protecting group without disruption of any other protecting groups present on the peptide chain. In this regard, it is preferred that the cleavage of the N-terminal protecting group be accomplished using trifluoroacetic acid. Generally, the cleavage will be carried out at a temperature from about 0° C. to about room temperature.

Once the N-terminal cleavage has been effected, the product which results normally will be in the form of the acid addition salt of the acid which has been employed to accomplish the cleavage of the protecting group. The product then can be converted to the free terminal amino compound by treatment with a mild base, typically a tertiary amine such as pyridine, triethylamine, or the like.

The peptide then is ready for reaction with the next succeeding amino acid. This can be accomplished by employing any of several recognized techniques. In order to achieve coupling of the next-succeeding amino acid to the N-terminal peptide chain, an amino acid which has a free carboxyl but which is suitably protected at the α-amino function as well as at any other active moiety is employed. The amino acid then is subjected to conditions which will render the carboxyl function active to the coupling reaction. One such activation technique which can be employed in the synthesis involves the conversion of the amino acid to a mixed anhydride. Thereby, the free carboxyl function of the amino acid is activated by reaction with another acid, typically a carbonic acid in the form of its acid chloride. Examples of such acid chlorides which can be used to form the appropriate mixed anhydrides are ethyl chloroformate, phenyl chloroformate, sec-butyl chloroformate, isobutyl chloroformate, pivaloyl, and the like.

Another method of activating the carboxyl function of the amino acid to achieve coupling is by conversion of the amino acid to its active ester derivative. Examples of such active esters are, for example, a 2,4,5-trichlorophenyl ester, a pentachlorophenyl ester, a 4-nitrophenyl ester, an ester formed from 1-hydroxybenzotriazole, and an ester formed from N-hydroxysuccinimide. Another method for effecting coupling of the C-terminal amino acid to the peptide fragment involves carrying out the coupling reaction in the presence of at least an equimolar quantity of N,N'-dicyclohexylcarbodiimide (DCC) or N,N'-diisopropylcarbodiimide. This latter method using N,N'-diisopropylcarbodiimide is preferred for preparing the tetradecapeptides of this invention with the exception that the asparagine residue is incorporated using its 4-nitrophenyl active ester.

By using the above described method of coupling followed by deprotection and starting with the above described α-amino deprotected cysteine-resin (i.e. H-Cys($R^2$)-O-$CH_2$-[resin] wherein $R^2$ is a sulfhydryl protecting group), the following protected amino acids are attached sequentially: $R^1$-Ser($R^5$) wherein $R^1$ is an α-amino protecting group and $R^5$ is a hydroxy protecting group; $R^1$-Thr($R^4$)-OH wherein $R^1$ is an α-amino protecting group and $R^4$ is a hydroxy protecting group; $R^1$-Phe-OH wherein $R^1$ is an α-amino protecting group; $R^1$-Thr($R^4$)-OH wherein $R^1$ is an α-amino protecting group and $R^4$ is a hydroxy protecting group; $R^1$-Lys($R^3$)-OH wherein $R^1$ is an α-amino protecting group and $R^3$ is an ε-amino protecting group; $R^1$-A-OH wherein A is as defined herein and $R^1$ is an α-amino proteting group; $R^1$-PHe-OH wherein $R^1$ is an α-amino protecting group; $R^1$-Phe-OH wherein $R^1$ is an α-amino protecting group; $R^1$-Asn-OH wherein $R^1$ is an α-amino protecting group; $R^1$-Lys($R^3$)-OH wherein $R^1$ is an α-amino protecting group and $R^3$ is an ε-amino protecting group; $R^1$-Cys($R^2$)-OH wherein $R^1$ is an α-amino protecting group and $R^2$ is a sulfhydryl protecting group; $R^1$-Gly-OH wherein $R^1$ is an α-amino protecting group; and $R^1$-Ala-OH wherein $R^1$ is an α-amino protecting group. In this manner the corresponding protected tetradecapeptide-resin of formula II, $R^1$-Ala-Gly-Cys($R^2$)-Lys($R^3$)-Asn-Phe-Phe-A-Lys($R^3$)-Thr($R^4$)-Phe-Thr($R^4$)-Ser($R^5$)-Cys($R^2$)-X in which A is as defined herein, $R^1$ is an α-amino protecting group, $R^2$ is a sulfhydryl protecting group, $R^3$ is an ε-amino protecting group, $R^4$ and $R^5$ each is a hydroxy protecting group and X is O-$CH_2$-[resin] is obtained.

Once the desired amino acid sequence has been prepared, the resulting peptide can be removed from the resin support. This is accomplished by treatment of the protected resin-supported tetradecapeptide with hydrogen fluoride. Treatment with hydrogn fluoride cleaves the peptide from the resin; in addition, however, it cleaves all remaining protecting groups present on the reactive moieties located on the peptide chain as well as the α-amino protecting group present at N-terminal amino acid. When hydrogen fluoride is employed to effect the cleavage of the peptide from the resin as well as removal of the protecting groups it is preferred that the reaction be carried out in the presence of anisole. The presence of anisole has been found to inhibit the potential alkylation of certain amino acid residues present in the peptide chain.

Once the cleavage reaction has been accomplished the product which is obtained is the corresponding straight-chain tetradecapeptide of formula II, H-Ala-Gly-Cys-Lys-Asn-Phe-Phe-A-Lys-Thr-Phe-Thr-Ser-Cys-OH in which A is as defined herein (in this formula: $R^1$, $R^2$, $R^3$, $R^4$ and $R^5$ are hydrogen and X is hydroxy). In order to obtain the final tetradecapeptides of this invention, it is necessary to treat the corresponding straight-chain tetradecapeptide under conditions which

the fractions corresponding to the main peak (fractions monitored at 300 nm). These fractions are lyophilized to give the corresponding tetradecapeptide of formula I in which A is as defined herein.

When a diasteromeric mixture of DL-tryptophan derivatives are used in the above described processes, a diastereomeric tetradecapeptide mixture will be present at this point. In fact, careful monitoring at 300 nm of the above partition chromatograph does show resolution of the diastereomers as partially resolved doublet. Each fraction is analyzed by high pressure liquid chromatography (HPLC), pooled separately according to the enrichment of the respective diastereomeric components and lyophilized. Each resulting fraction is then subjected to another partition chromatography on a Sephadex ™ G-25 column using 1-butanol-2 M acetic acid (1:1 v/v) and monitoring the eluate at 280 nm. This monitoring shows that the main peak is separated from the smaller peak corresponding to the contaminating diasteromer with little or no overlap. The column fractions are checked by HPLC to serve as a guide for pooling the peaks to ensure isolation of pure components. The pooled fractions are lyophilized to give a powder of the corresponding tetradecapeptide of formula I

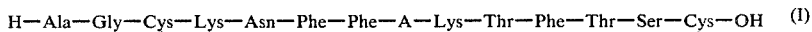

will effect its oxidation by converting the two sulfhydryl groups present in the molecule, one at each cysteinyl moiety, to a disulfide bridge. This can be accomplished by treating a dilute solution of the linear tetradecapeptide with any of a variety of oxidizing agents including, for example, iodine, potassium fericyanide, oxygen and the like. Air also can be employed as oxidizing agent, the pH of the mixture generally being from about 2.5 to about 9.0, and preferably from about 7.0 to about 7.6. The concentration of the solution which is employed generally is not greater than about 0.4 mg. of the peptide per milliliter of solution, and usually is about 50 μg/ml. The preferred method of oxidative cyclization is with an aqueous solution of potassium ferricyanide buffered to pH 7.1 at room temperature for 10 to 30 minutes preferably for 20 minutes. The ferri- and ferrocyanide salts are readily removed by adding a Dowex ™ AG3 X 4A resin (chloride form) and filtering the mixture. The filtrate is then lyophilized. At this point, it is also desirable to remove other contaminating salts by gel filtration. The preferred method of gel filtration is to dissolve the lyophilized material in 50% acetic acid and pass the solution through a column of Sephadex ™ G-15. The eluates are lyophilized and subjected to another gel filtration by dissolving the lyophilized material in 0.2 M acetic acid and passing the solution through a column of Sephadex ™ G-25. The eluates are lyophilized and the resulting powder is subjected to partition chromatography to remove peptide impurities. A preferred method to remove peptide impurities is to subject the latter lyophilized powder to partition chromatography on a column of Sephadex ™ G-15 using 1-butanolacetic acid-water (4:1:5 v/v) and collecting in which A represents D or L 5- or 6-fluoro-, bromo-, chloro- or iodotryptophyl.

Lyophilization of the latter tetradecapeptide from 0.1 M acetic acid affords the tetradecapeptide as the acetate salt which can be converted to the corresponding free base by repeated lyophilization from water.

The following Examples illustrates further this invention.

EXAMPLE 1 t-Butoxycarbonyl-DL-5-bromotryptophan

DL-5-Bromotryptophan is converted using the method described by D. H. Coy et al., Biochemistry, 13, 3550(1974), herein incorporated by reference, to obtain the title compound (81% yield); mp 157°–159° C.

Anal. Calc'd for $C_{16}H_{19}O_4N_2Br$: C, 50,14; H, 5.00; N, 7.13%. Found: C, 50.34; H, 5.18; N, 7.27%.

Similarity, DL-5-fluorotryptophan is converted to t-butoxycarbonyl-DL-5-fluorotryptophan (80% yield): mp 157°–158° C.

DL-6-Fluorotryptophan is converted using the method described by A. Ali et al., Angew Chem., 84, 259(1972), herein incorporated by reference, to obtain t-butoxycarbonyl-DL-6-fluorotryptophan (59% yield); mp 127°–129° C.

Anal. Calc'd for $C_{16}H_{19}O_4N_2F$: C, 59.62; H, 5.94; N, 8.69%. Found: C, 59.80; H, 6.12; N, 8.63%.

EXAMPLE 2 t-Butoxycarbonyl-L-alanyl-glycyl-L-(S-4-methylbenzyl)cysteinyl-L-(N$^6$-2-chlorobenzyloxycarbonyl)lysyl-L-asparaginyl-L-phenylalanyl-L-phenylalanyl-DL-5-bromotryptophyl-L-(N$^6$-2-chlorobenzyloxycarbonyl)lysyl-L-(O-benzyl)threonyl-L-phenylalanyl-L-(O-benzyl)threonyl-L-seryl-L-(O-benzyl)seryl-L-(S-4-methylbenzyl)cysteinyl resin To the 300 ml reaction vessel of a Beckman 990 automatic peptide synthesizer is added 3.00 g (0.76 mmole) of t-butoxycarbonyl-L-(S-4-methylbenzyl)cysteine resin, prepared from a polystyrene, 1% divinylbenzene resin, i.e. the degree of cross linking of the polystyrene with divinylbenzene is 1%, in the same manner as described by B. F. Gisin, Helv. Chim. Acta, 56, 1476–1482(1973), herein incorporated by reference, and the resin is washed with methylene chloride (45 ml), three times, ethanol (45 ml), three times, and chloroform (45 ml), three times, allowing a contact time of at least 3 minutes each. The peptide resin is then subjected to ninhydrin test following the procedure of E. Kaiser et al., Analytical Biochemistry, 34, 595(1970). It should be negative at this stage.

The deprotection of the α-amino protecting group from t-butoxycarbonyl-L-(S-4-methylbenzyl)cysteine resin is carried out as follows: the peptide resin is treated with a 1:3 solution of trifluoroacetic acetic acid in methylene chloride for 5 minutes, filtered and again for 25 minutes and filtered. The peptide resin is then put through the following wash cycle: (a) chloroform (45 ml), three times; (b) ethanol (45 ml), three times; (c) methylene chloride (45 ml), three times; (d) 10% triethylamine in chloroform (45 ml), two times each for 10 minutes; (e) chloroform (45 ml), three times; and methylene chloride (45 ml), three times. Each washing step takes 1.5 minutes.

The resulting resin is gently mixed with t-butoxycarbonyl-L-(O-benzyl)serine (3 mmoles) in methylene chloride (22 ml) for 1.5 minutes and a solution of diisopropylcarbodiimide (3 mmoles) in methylene chloride (10 ml) is added. Mixing is continued at room temperature for 120 minutes and the peptide resin is washed with methylene chloride (45 ml), three times; ethanol (45 ml), three times and chloroform (45 ml), three times. To test for completeness of reaction, the peptide resin is subjected to a ninhydrin test as described by E. Kaiser et al., cited above. If a positive ninhydrin test is indicated, the coupling reaction is repeated using the appropriate symmetric anhydride, prepared as described by J. Blake and C. H. Li, Int. J. Peptide Protein Res., 8, 589(1976), herein incorporated by reference, but in dimethylformamide at room temperature. Any remaining free amino groups are acetylated with acetic anhydride or acetyl imidazole.

The removal of the α-amino protecting group at each step is performed as described for the deprotection of the t-butoxycarbonyl-L-(S-4-methylbenzyl)cysteine resin.

The following amino acid residues are then introduced sequentially by coupling and deprotection in the same manner as described above (BOC means butoxycarbonyl): t-Boc-L-(O-benzyl)threonine, (3 mmoles; and 3 mmoles of diisopropylcarbodiimide), t-BOC-L-phenylalanine (3 mmoles; and 3 mmoles of diisopropylcarbodiimide), t-BOC-L-(O-benzyl)threonine (3 mmoles; and 3 mmoles of diisopropylcarbodiimide); t-BOC-L-(N$^6$-2-chlorobenzyloxycarbonyl)lysine (3 mmoles; and 3 mmoles of diisopropylcarbodiimide); t-BOC-DL-5-bromotryptophan (3 mmoles; and 3 mmoles of diisopropylcarbodiimide, described in Example 1); t-BOC-L-phenylalanine (3 mmoles; and 3 mmoles of diispropyl-carbodiimide); t-BOC-L-phenylalanine (3 mmoles; and 3 mmoles of diisopropylcarbodiimide), t-BOC-L-asparagine-4-nitrophenyl ester (5 mmoles in Dimethyl-formamide and the coupling is allowed to proceed for 12 hours), t-BOC-L-(N$^6$-2-chlorobenzyloxy)lysine (3 mmoles; and 3 mmoles of diisopropylcarbodiimide), t-BOC-L-(S-4-methylbenzyl)cysteine (3 mmoles; and 3 mmoles of diisopropylcarbodiimide), t-Boc-glycine (3 mmoles; and 3 mmoles of diisopropylcarbodiimide), and t-BOC-L-alanine (3 mmoles; and 3 mmoles of diisopropylcarbodiimide). At the end of the synthesis the cream-coloured resin is washed with methanol, removed from the reactor and dried to give a powder of the title peptide-resin.

EXAMPLE 3

L-Alanyl-glycyl-L-cysteinyl-L-lysyl-L-asparaginyl-L-phenylalanyl-L-phenylalanyl-DL-5-bromotryptophyl-L-lysyl-L-threonyl-L-phenylanyl-L-threonyl-L-seryl-L-cysteine A mixture of the tetradecapeptide-resin of Example 2 (2.0 g) and a solution of 10% anisole in hydrogen fluoride (40 ml) is stirred at 0° C. for 1 hour. Excess hydrogen fluoride is evaporated as quickly as possible under reduced pressure and the residue is washed free of anisole with a large volume of ethyl acetate. The remaining residue is a mixture of the title compound and the resin. If desired, the residue can be dissolved in degassed 10% acetic acid and the solution is filtered and lyophilized to obtain title compound as a powder.

EXAMPLE 4

Cyclic[3-14 Disulfide] of L-Alanyl-glycyl-L-cysteinyl-L-lysyl-L-asparaginyl-L-phenylalanyl-L-phenylalanyl-DL-5-bromotryptophyl-L-lysyl-L-threonyl-L-phenylalanyl-L-threonyl-L-seryl-L-cysteine([DL-5-Br-Trp]$^8$-somatostatin: I; A=DL-5-bromotryptophyl)

The residue of Example 3 containing the title compound of Example 3 and the resin is extracted with 200 ml of 2 M acetic acid. The frothy solution is diluted to a volume of 500 ml with water, adjusted to pH 7.1 with ammonium hydroxide and an aqueous solution of potassium ferricyanide (50 ml, 0.01 M) is added. After stirring for 20 minutes, the pH is readjusted to 5 and Dowex TM AG3 X 4A resin (chloride form) is introduced to remove ferri- and ferrocyanide salts. The mixture is filtered and the filtrate is lyophilized. The residue is subjected to gel filtration on a column (2.5×95 cm) of Sephadex TM G-15 using 50% acetic acid and the eluates are lyophilized followed by another gel filtration on a column (2.5×95 cm) of Sephadex TM G-25 using 0.2 M acetic acid. Lyophilization of the eluate gives the title compound as a powder.

EXAMPLE 5

Cyclic[3-14 Disulfide] of
L-Alanyl-glycyl-L-cysteinyl-L-lysyl-L-asparaginyl-L-phenylalanyl-L-phenylalanyl-D-5-bromotryptophyl-L-lysyl-L-threonyl-L-phenylalanyl-L-threonyl-L-seryl-L-cysteine([D-5-Br-Trp]$^8$-somatostatin: I;
A=D-5-bromotryptophyl)

The title tetradecapeptide of Example 4, [DL-5-Br-Trp]$^8$-somatostatin, is subjected to partition chromatography on a Sephadex ™ G-25 column (2.5×95 cm) using the solvent 1-butanol:acetic acid:water (4:1.5, v/v) and fractions of 10 ml are collected. The fractions corresponding to the main peaks of a partially resolved doublet (300 nm) are pooled separately, concentrated under under reduced pressure and lyophilized. The mixtures, significantly enriched in their diastereomeric components, and free of other components as judged by HPLC (Waters Assoc. Model 204 liquid chromatograph equipped with two Model 6000 A pumps and a Model 660 gradient programmer; by reversed-phase high pressure liquid chromatography on a column (0.4×25 cm) of $C_{18}\mu$-Bondapack at 220 and 280 nm and using as solvent a mixture of the following systems: 10% acetonitrile in 0.01 N ammonium acetate, pH 4.1 (A) and 90% acetonitrile in the same ammonium acetate buffer; conditions are: (1) linear gradient from a mixture of 90% A, 10% B (containing 1% N-ethylmorpholine) to 60% A, 40% B over 20 min; (2) linear gradient from a mixture of 90% A, 10% B to 50% A, 50% B over 10 min; and (3) continuous mixture of 40% A, 60% B; and the flow rate is 1.5 ml per min) are separately passed through a Sephadex ™ G-25 partition column (1.5×140 cm) using 1-butanol:2 M acetic acid (1:1 v/v). In each case, the main peak (280 nm) is separated from a single smaller peak corresponding to the contaminating diastereomer with little or no overlap. HPLC of the column fractions are used as a guide to separately pool the peaks to ensure isolation of pure components. Pooled fractions are concentrated under reduced pressure and lyophilized to give the title tetradecapeptide: yields and $R_F$ mobility are reported in Table II; optical rotation and absorption maxima are reported in Table III and amino acid analysis is reported in Table IV. Enzymatic hydrolysis: the title compound (150 µg) is incubated for 16 hours at 37° C. with aminopeptidase M (15 µg) in 0.2 N N-ethylmorpholine acetate, pH 8.1 (100 µl) according to the method described in Biol. Chem., 247, 2704(1972). Digests are acidified with one drop of acetic acid, frozen, lyophilized, and aliquots are removed for amino acid analysis, which are reported in Table V.

Other pooled fractions are concentrated under reduced pressure and lyophilized to give the cyclic[3-14 disulfide] of L-alanyl-glycyl-L-cysteinyl-L-lysyl-L-asparaginyl-L-phenylalanyl-L-phenylalanyl-L-5-bromotryptophyl-L-lysyl-L-threonyl-L-phenylalanyl-L-threonyl-L-seryl-L-cysteine([L-5-Br-Trp]$^8$-somatostatin: 1; A=L-5-bromotryptophyl), analytical results are reported in Tables II, III, IV and V.

EXAMPLE 6

Replacing t-BOC-DL-5-bromotryptophan in Example 2 with an equivalent amount of t-BOC-DL-6-fluorotryptophan (described in Example 1) and repeating the procedure of Examples 2, 3, 4 and 5, the following tetradecapeptide somatostatin analogs are obtained: cyclic[3-14 disulfide] of L-alanyl-glycyl-L-cysteinyl-L-lysyl-L-asparaginyl-L-phenylalanyl-L-phenylalanyl-D-6-fluorotryptophyl-L-lysyl-L-threonyl-L-phenylalanyl-L-threonyl-L-seryl-L-cysteine([D-6-F-Trp]$^8$-somatostatin: 1; A=D-6-fluorotryptophyl), analytical results are reported in Tables II, III, IV and V; and cyclic[3-14 disulfide] of L-alanyl-glycyl-L-cysteinyl-L-lysyl-L-asparaginyl-L-phenylalanyl-L-phenylalanyl-L-6-fluorotryptophyl-L-lysyl-L-threonyl-L-phenylalanyl-L-threonyl-L-seryl-L-cysteine([L-6-F-Trp]$^8$-somatostatin: (1; A=L-6-fluorotryptophyl), analytical results are reported in Tables II, III, IV and V.

EXAMPLE 7

Replacing t-BOC-DL-5-bromotryptophan in Example 2 with an equivalent amount of t-BOC-DL-5-fluorotryptophan (described in Example 1) and repeating the procedure of Example 2, 3, 4 and 5, the following tetradecapeptide somatostatin analogs are obtained: cyclic[3-14 disulfide] of L-alanyl-glycyl-L-cysteinyl-L-lysyl-L-asparaginyl-L-phenylalanyl-L-phenylalanyl-D-5-fluorotryptophyl-L-lysyl-L-threonyl-L-phenylalanyl-L-threonyl-L-seryl-L-cysteine([D-5-F-Trp]$^8$-somatostatin: 1; A=D-5-fluorotryptophyl), analytical results are reported in Tables II, III, IV and V; and cyclic[3-14 disulfide] of L-alanyl-glycyl-L-cysteinyl-L-asparaginyl-L-lysyl-L-phenylalanyl-L-phenylalanyl-L-5-fluorotryptophyl-L-lysyl-L-threonyl-L-phenylalanyl-L-threonyl-L-seryl-L-cysteine([L-5-F-Trp]$^8$-somatostatin: 1; A=L-5-fluorotryptophyl), analytical results are reported in Tables II, III, IV and V.

EXAMPLE 8

Replacing t-BOC-DL-5-bromotryptophan in Example 2 with an equivalent amount of t-BOC-L-5-fluorotryptophan (described by D. H. Coy et al., (1974), cited above) and repeating the procedure of Examples 2, 3, 4 and 5, the following tetradecapeptide somatostatin analog is obtained: cyclic[3-14 disulfide] of L-alanyl-glycyl-L-cysteinyl-L-lysyl-L-asparaginyl-L-phenylalanyl-L-phenylalanyl-L-5-fluorotryptophyl-L-lysyl-L-threonyl-L-phenylalanyl-L-threonyl-L-seryl-L-cysteine([L-5-F-Trp]$^8$-somatostatin: 1; A=L-5-fluorotryptophyl), analytical results are reported in Tables II, III, IV and V.

TABLE II

PROPERTIES OF SOMATOSTATIN ANALOGS

| Substituent in Position 8 | Described in Ex. | Yield[a] (%) | $R_f(I)$[b] | $R_f(II)$ | $R_f(III)$ | $R_f(IV)$ |
|---|---|---|---|---|---|---|
| L-5Br-Trp | 5 | 13 | 0.08 | 0.36 | 0.38 | 0.59 |
| D-5Br-Trp | 5 | 9 | 0.07 | 0.35 | 0.38 | 0.56 |
| L-6F-Trp | 6 | 14 | 0.08 | 0.36 | 0.38 | 0.59 |
| D-6F-Trp | 6 | 11 | 0.07 | 0.36 | 0.38 | 0.57 |
| L-5F-Trp | 7 | 18 | 0.07 | 0.36 | 0.37 | 0.58 |
| D-5F-Trp | 7 | 12 | 0.07 | 0.35 | 0.37 | 0.55 |
| L-5F-Trp | 8 | 11 | 0.07 | 0.36 | 0.37 | 0.58 |

[a]Yields based on final products compared to total mM of starting BOC-amino acid esterified to the resin.
[b]The following TLC solvent systems were used: $R_f(I)$, n-BuOH-AcOH-H$_2$O (4:1:5, upper phase), $R_f(II)$, i-PrOH-1M AcOH (2:1); $R_f(III)$, n-BuOH-AcOH-H$_2$O-EtOAc (1:1:1:1); $R_f(IV)$, EtOAc-Pyridine-AcOH-H$_2$O (5:5:1:3). Samples (20-40µg) were applied to Brinkman SIL-G25 plates and solvent fronts allowed to travel 10-15cm. Spot were visualized with ninhydrin and Ehrlich's reagents.

TABLE III

ABSORPTION MAXIMA (λ max) AND OPTICAL ROTATION of SOMATOSTATIN ANALOGS[a]

| Substituent in Position 8 | Described in Example | [α]$_D$ (deg) in 0.1M AcOH | λ max (nm) |
|---|---|---|---|
| L-5Br-Trp | 5 | −31(c0.61,25°) | 289 |
| D-5Br-Trp | 5 | −36(c0.56,23°)[b] | 289 |
| L-6F-Trp | 6 | −40(c0.55,23°) | 281 |
| D-6F-Trp | 6 | −43(c0.52,24°) | 281 |
| L-5F-Trp | 7 | −32(c0.50,25°) | 285 |
| D-5F-Trp | 7 | −44(c0.50,26°) | 285 |
| L-5F-Trp | 8 | −36(c0.50,26°) | |

[a]Peptide samples (1.3 × 10$^{-4}$M) in 0.1M AcOH are read from 275-295nm at 1nm intervals.
[b]50% AcOH was used as the solvent.

TABLE IV

AMINO ACID ANALYSES OF ACID HYDROLYZED SOMATOSTATIN ANALOGS[a]

| Substituent in Position 8 | Described in Example | Ala | Gly | ½Cys | Lys | Asp | Phe | A | Thr | Ser | NH$_3$ |
|---|---|---|---|---|---|---|---|---|---|---|---|
| L-5Br-Trp | 5 | 1.00 | 1.00 | 1.92 | 1.97 | 1.04 | 3.00 | b | 1.94 | 0.89 | 1.35 |
| D-5Br-Trp | 5 | 0.99 | 1.00 | 1.88 | 1.91 | 1.04 | 2.97 | b | 2.00 | 0.95 | 1.34 |
| L-6F-Trp | 6 | 1.00 | 1.03 | 1.98 | 1.94 | 1.03 | 3.05 | 0.97 | 1.93 | 0.87 | 1.31 |
| D-6F-Trp | 6 | 1.00 | 1.02 | 1.87 | 1.93 | 1.05 | 3.01 | 1.04 | 2.00 | 0.97 | 1.39 |
| L-5F-Trp | 7 | 1.00 | 1.02 | 1.95 | 1.94 | 1.02 | 3.05 | 1.04 | 1.96 | 0.91 | 1.32 |
| D-5F-Trp | 7 | 0.98 | 1.00 | 1.77 | 1.91 | 1.02 | 2.94 | 1.01 | 1.97 | 0.94 | 1.42 |
| L-5F-Trp | 8 | 1.00 | 1.00 | 1.80 | 2.06 | 0.94 | 3.08 | 0.96 | 1.96 | 0.88 | 1.03 |

[a]Samples are hydrolyzed in 4N methanesulfonic acid containing 0.2% 3-(2-aminoethyl) indole at 110° C. for 18 hr in sealed evacuated tubes.
[b]Not eluted under standard analyzer conditions.

TABLE V

AMINO ACID ANALYSES OF ENZYMATICALLY HYDROLYZED SOMATOSTATIN ANALOGS

| Substituent in Position 8 | Described in Example | Ala | Gly | ½Cys | Lys | Asn + Ser | Phe | A | Thr | NH$_3$ |
|---|---|---|---|---|---|---|---|---|---|---|
| L-5Br-Trp | 5 | 1.10 | 1.00 | 1.74 | 1.84 | 1.76 | 2.75 | a | 1.89 | 0.11 |
| D-5Br-Trp | 5 | 1.00 | 0.69 | — | 0.16 | 0.18 | 0.15 | a | — | — |
| L-6F-Trp | 6 | 1.06 | 1.00 | 1.62 | 1.73 | 1.53 | 2.60 | 0.89 | 1.83 | 0.11 |
| D-6F-Trp | 6 | 1.07 | 1.00 | 0.91 | 0.57 | 0.85 | 0.68 | — | — | 0.13 |
| L-5F-Trp | 7 | 1.22 | 1.00 | 1.53 | 1.69 | 1.42 | 2.49 | 0.62 | 1.87 | 0.14 |
| D-5F-Trp | 7 | 1.00 | 0.54 | 0.04 | 0.21 | 0.14 | 0.13 | — | — | 0.14 |

[a]Not eluted under standard analyzer conditions.

We claim:
1. A tetradecapeptide of the formula

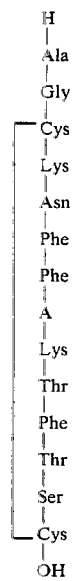

in which A represents L, D or DL 5- or 6- fluoro-, bromo-, chloro- or iodo-tryptophyl, or a therapeutically acceptable acid addition salt thereof.

2. A tetradecapeptide of the formula

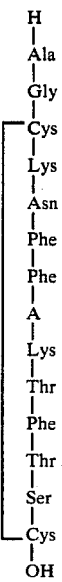

in which A represents L or D 5- or 6- fluoro- or bromo-tryptophyl, or a therapeutically acceptable acid addition salt thereof.

3. The tetradecapeptide of claim 2 which is cyclic[3-14-disulfide] of L-alanyl-glycyl-L-cysteinyl-L-lysyl-L-asparaginyl-L-phenylalanyl-L-phenylalanyl-L-5-bromotryptophyl-L-lysyl-L-threonyl-L-phenylalanyl-L-threonyl-L-seryl-L-cysteine.

4. The tetradecapeptide of claim 2 which is cyclic[3-14 disulfide] of L-alanylglycyl-L-cysteinyl-L-lysyl-L-asparaginyl-L-phenylalanyl-L-phenylalanyl-D-5-bromotryptophyl-L-lysyl-L-threonyl-L-phenylalanyl-L-threonyl-L-seryl-L-cysteine.

5. The tetradecapeptide of claim 2 which is cyclic[3-14 disulfide] of L-alanyl-glycyl-L-cysteinyl-L-lysyl-L-asparaginyl-L-phenylalanyl-L-phenylalanylL-6-fluoro-tryptophyl-L-lysyl-L-threonyl-L-phenylalanyl-L-threonyl-L-seryl-cysteine.

6. The tetradecapeptide of claim 2 which is cyclic[3-14 disulfide] of L-alanyl-glycyl-L-cysteinyl-L-lysyl-L-asparaginyl-L-phenylalanyl-L-phenylalanyl-D-6-fluoro-tryptophyl-L-lysyl-L-threonyl-L-phenylalanyl-L-threonyl-L-seryl-L-cysteine.

7. The tetradecapeptide of claim 2 which is cyclic[3-14 disulfide] of L-alanyl-glycyl-L-cysteinyl-L-lysyl-L-asparaginyl-L-phenylalanyl-L-phenylalanyl-L-5-fluoro-tryptophyl-L-lysyl-L-threonyl-L-phenylalanyl-L-threonyl-L-seryl-L-cysteine.

8. The tetradecapeptide of claim 2 which is cyclic[3-14 disulfide] of L-alanyl-glycyl-L-cysteinyl-L-lysyl-L-asparaginyl-phenylalanyl-L-phenylalanyl-D-5-fluoro-tryptophyl-L-lysyl-L-threonyl-L-phenylalanyl-L-threonyl-L-seryl-L-cysteine.

9. The tetradecapeptide of claim 1 which is cyclic[3-14 disulfide] of L-alanyl-glycyl-L-cysteinyl-L-lysyl-L-asparaginyl-L-phenylalanyl-L-phenylalanyl-DL-5-bromotryptophyl-L-lysyl-L-threonyl-L-phenylalanyl-L-threonyl-L-seryl-L-cysteine.

10. The tetradecapeptide of claim 1 which is cyclic[3-14 disulfide] of L-alanyl-glycyl-L-cysteinyl-L-lysyl-L-asparaginyl-L-phenylalanyl-L-phenylalanyl-DL-6-fluorotryptophyl-L-lysyl-L-threonyl-L-phenylalanyl-L-threonyl-L-seryl-L-cysteine.

11. The tetradecapeptide of claim 1 which is cyclic[3-14 disulfide] of L-alanyl-glycyl-L-cysteinyl-L-lysyl-L-asparaginyl-L-phenylalanyl-L-phenylalanyl-DL-5-fluorotryptophyl-L-lysyl-L-threonyl-L-phenylalanyl-L-threonyl-L-seryl-L-cysteine.

12. A peptide of the formula $R^1$-Ala-Gly-Cys($R^2$)-Lys($R^3$)-Asn-Phe-Phe-A-Lys($R^3$)-Thr($R^4$)-Phe-Thr($R^4$)-Ser($R^5$)-Cys($R^2$)-X in which A represents L, D or DL 5- or 6- fluoro-, bromo-, chloro- or iodo- tryptophyl; $R^1$ is hydrogen or an α-amino protecting group; $R^2$ is hydrogen or a sulfhydryl protecting group $R^3$ is hydrogen or an ε-amino protecting group; $R^4$ and $R^5$ each is hydrogen or a hydroxy protecting group; and X is hydroxy or O—$CH_2$—[resin], with the proviso that: when X is hydroxy, then $R^1$, $R^2$, $R^3$, $R^4$ and $R^5$ are hydrogen; and when X is O—$CH_2$—[resin], then $R^1$, $R^2$, $R^3$, $R^4$ and $R^5$ each are other than hydrogen.

13. A peptide as claimed in claim 12 wherein A is as defined therein; $R^1$, $R^2$, $R^3$, $R^4$ and $R^5$ are hydrogen; and X is hydroxy.

14. A peptide as claimed in claim 12 wherein A represents L, D or DL 5- or 6- fluoro- or bromo- tryptophyl; $R^1$ is hydrogen or t-butoxycarbonyl; $R^2$ is hydrogen or 4-methylbenzyl; $R^3$ is hydrogen or 2-chlorobenzyloxycarbonyl; $R^4$ and $R^5$ each is hydrogen or benzyl; and X is hydroxy or O-$CH_2$-[polystyrene-1%-divinylbenzene resin], with the proviso that: when X is hydroxy, then $R^1$, $R^2$, $R^3$, $R^4$ and $R^5$ are hydrogen; and when X is O-$CH_2$-[polystyrene-1%-divinylbenzene resin], then $R^1$, $R^2$, $R^3$, $R^4$ and $R^5$ are other than hydrogen.

15. A peptide as claimed in claim 12 wherein A represents L, D or DL 5- or 6- fluoro- or bromo- tryptophyl; $R^1$, $R^2$, $R^3$, $R^4$ and $R^5$ are hydrogen; and X is hydroxy.

16. A pharmaceutical composition which comprises a compound of claim 1 or a therapeutically acceptable acid addition salt thereof and a pharmaceutically acceptable liquid or solid carrier therefor.

17. A method of treating acromegaly or of managing diabetes in a mammal, which comprises administering to said mammal an effective dose of a compound of claim 1 or a therapeutically acceptable acid addition salt thereof.

* * * * *